US009726667B2

(12) United States Patent
Moritz et al.

(10) Patent No.: US 9,726,667 B2
(45) Date of Patent: Aug. 8, 2017

(54) POINT OF CARE ASSAYS TO DETECT THE STATUS OF TUBERCULOSIS INFECTION

(71) Applicant: Institute for Systems Biology, Seattle, WA (US)

(72) Inventors: Robert L. Moritz, Seattle, WA (US); Mark Sartain, Seattle, WA (US); Zdenek Spacil, Seattle, WA (US); Ulrike Kusebauch, Seattle, WA (US); David Campbell, Seattle, WA (US)

(73) Assignee: INSTITUTE FOR SYSTEMS BIOLOGY, Seattle, WA (US)

( * ) Notice: Subject to any disclaimer, the term of this patent is extended or adjusted under 35 U.S.C. 154(b) by 18 days.

(21) Appl. No.: 14/641,152

(22) Filed: Mar. 6, 2015

(65) Prior Publication Data
US 2015/0253324 A1 Sep. 10, 2015

Related U.S. Application Data

(60) Provisional application No. 61/984,606, filed on Apr. 25, 2014, provisional application No. 61/949,857, filed on Mar. 7, 2014.

(51) Int. Cl.
*C12Q 1/68* (2006.01)
*G01N 33/53* (2006.01)
*G01N 33/567* (2006.01)
*G01N 33/554* (2006.01)
*G01N 33/569* (2006.01)
*G01N 33/00* (2006.01)

(52) U.S. Cl.
CPC .......... *G01N 33/5695* (2013.01); *G01N 33/00* (2013.01)

(58) Field of Classification Search
CPC .. C07K 14/35; G01N 33/53; G01N 33/56911; G01N 33/5695; G01N 21/64; G01N 21/6486; G01N 2469/20; G01N 2800/52
See application file for complete search history.

(56) References Cited

U.S. PATENT DOCUMENTS

| 2004/0110269 | A1 | 6/2004 | Vipond et al. |
| 2008/0171345 | A1* | 7/2008 | Belisle ............... G01N 33/5695 435/7.32 |
| 2009/0280140 | A1 | 11/2009 | Laal et al. |
| 2011/0268744 | A1 | 11/2011 | Garthwaite et al. |

FOREIGN PATENT DOCUMENTS

WO     WO 03/012395     *  2/2003  ............. C07K 14/35

OTHER PUBLICATIONS

Invitation to Pay Additional Fees for PCT/US15/19285, mailed Jul. 1, 2015, 2 pages.
(Continued)

*Primary Examiner* — Ja'na Hines
(74) *Attorney, Agent, or Firm* — Morrison & Foerster LLP

(57) ABSTRACT

Point of care methods to detect the probability or status of tuberculosis infection in individuals by determining presence or absence of one or more peptide of SEQ ID NOS: 1-22 in a biological fluid of a subject are described. These methods may be assays based on affinity reagents specifically reactive with these peptides.

12 Claims, 3 Drawing Sheets

(56) References Cited

OTHER PUBLICATIONS

Kashino et al., "Identification and characterization of *Mycobacterium tuberculosis* antigens in urine of patients with active pulmonary tuberculosis: an innovative and alternative approach of antigen discovery of useful microbial molecules," Clinical and Experimental Immunology (2008) 153:56-62.

Napolitano et al., "Identification of *Mycobacterium tuberculosis* ornithine carboamyltransferase in urine as a possible molecular marker of active pulmonary tuberculosis," Clinical and Vaccine Immunology (2008) 15(4):638-643.

International Search Report and Written Opinion for PCT/US15/19285, mailed Sep. 4, 2015, 12 pages.

UniProtKB entry F9UUP4 (Oct. 19, 2011), 1 page.

\* cited by examiner

SEQUENCE LISTING

```
<160> NUMBER OF SEQ ID NOS: 22

<210> SEQ ID NO 1
<211> LENGTH: 17
<212> TYPE: PRT
<213> ORGANISM: Homo sapiens

<400> SEQUENCE: 1

Ala Glu Ser Asp Asp Leu Asp Ala Leu Val Ala His Leu Pro Ala Asp
1               5                   10                  15

Arg

<210> SEQ ID NO 2
<211> LENGTH: 11
<212> TYPE: PRT
<213> ORGANISM: Homo sapiens

<400> SEQUENCE: 2

Ala Ala Pro Ala Thr Val Ser Glu Leu Asp Arg
1               5                   10

<210> SEQ ID NO 3
<211> LENGTH: 10
<212> TYPE: PRT
<213> ORGANISM: Homo sapiens

<400> SEQUENCE: 3

Ala Leu Glu Ile Val Asp Ala Leu Pro Arg
1               5                   10

<210> SEQ ID NO 4
<211> LENGTH: 7
<212> TYPE: PRT
<213> ORGANISM: Homo sapiens

<400> SEQUENCE: 4

Met Cys Val Leu Thr Gly Lys
1               5

<210> SEQ ID NO 5
<211> LENGTH: 10
<212> TYPE: PRT
<213> ORGANISM: Homo sapiens

<400> SEQUENCE: 5

Asn Phe Tyr Asp Ala Asp Pro Leu Ala Lys
1               5                   10

<210> SEQ ID NO 6
<211> LENGTH: 9
<212> TYPE: PRT
```

<213> ORGANISM: Homo sapiens

<400> SEQUENCE: 6

Val Glu Leu Asp Asp Leu Leu His Lys
1               5

<210> SEQ ID NO 7
<211> LENGTH: 13
<212> TYPE: PRT
<213> ORGANISM: Homo sapiens

<400> SEQUENCE: 7

Phe Ser Ile Gly Thr Asn Thr Ile Gly Thr Glu Ser Arg
1               5                   10

<210> SEQ ID NO 8
<211> LENGTH: 7
<212> TYPE: PRT
<213> ORGANISM: Homo sapiens

<400> SEQUENCE: 8

Asp Ser Val Asp Asp Ile Arg
1               5

<210> SEQ ID NO 9
<211> LENGTH: 12
<212> TYPE: PRT
<213> ORGANISM: Homo sapiens

<400> SEQUENCE: 9

Ala Phe Glu Ala Gly Glu Pro Gln Ala Ser Gly Lys
1               5                   10

<210> SEQ ID NO 10
<211> LENGTH: 7
<212> TYPE: PRT
<213> ORGANISM: Homo sapiens

<400> SEQUENCE: 10

Val Tyr Thr Thr Thr Pro Lys
1               5

<210> SEQ ID NO 11
<211> LENGTH: 11
<212> TYPE: PRT
<213> ORGANISM: Homo sapiens

<400> SEQUENCE: 11

Asp Ile Ile Leu Ala Pro Val Ile Ser Glu Lys
1               5                   10

<210> SEQ ID NO 12
<211> LENGTH: 8
<212> TYPE: PRT
<213> ORGANISM: Homo sapiens

<400> SEQUENCE: 12

Leu Gly Glu Phe Ala Pro Thr Arg
1               5

<210> SEQ ID NO 13
<211> LENGTH: 10
<212> TYPE: PRT
<213> ORGANISM: Homo sapiens

```
<400> SEQUENCE: 13

Ala Thr Glu Tyr Pro Ser Ala Val Ala Lys
1               5                   10

<210> SEQ ID NO 14
<211> LENGTH: 7
<212> TYPE: PRT
<213> ORGANISM: Homo sapiens

<400> SEQUENCE: 14

Glu Glu Leu Phe Asn Leu Arg
1               5

<210> SEQ ID NO 15
<211> LENGTH: 7
<212> TYPE: PRT
<213> ORGANISM: Homo sapiens

<400> SEQUENCE: 15

Asp Trp Leu Val Ser Ala Arg
1               5

<210> SEQ ID NO 16
<211> LENGTH: 13
<212> TYPE: PRT
<213> ORGANISM: Homo sapiens

<400> SEQUENCE: 16

Val Ala Gly Cys Asp Gln Ala Ala Val Tyr Ala Pro Lys
1               5                   10

<210> SEQ ID NO 17
<211> LENGTH: 13
<212> TYPE: PRT
<213> ORGANISM: Homo sapiens

<400> SEQUENCE: 17

Leu Ser Asp Ser Pro Leu Gln Val Thr Ile Trp Thr Lys
1               5                   10

<210> SEQ ID NO 18
<211> LENGTH: 9
<212> TYPE: PRT
<213> ORGANISM: Homo sapiens

<400> SEQUENCE: 18

Glu Leu Ala Gly Thr Phe Ser Ala Arg
1               5

<210> SEQ ID NO 19
<211> LENGTH: 10
<212> TYPE: PRT
<213> ORGANISM: Homo sapiens

<400> SEQUENCE: 19

Val Ser Ala Glu Leu Ile Thr Ala Ala Arg
1               5                   10

<210> SEQ ID NO 20
<211> LENGTH: 18
<212> TYPE: PRT
<213> ORGANISM: Homo sapiens

<400> SEQUENCE: 20
```

-continued

```
Ser Phe Cys Ala Leu Gly Asp Gly Ala Ala Ser Pro Val Met Ser Ser
1               5                   10                  15

Ile Lys

<210> SEQ ID NO 21
<211> LENGTH: 9
<212> TYPE: PRT
<213> ORGANISM: Homo sapiens

<400> SEQUENCE: 21

Val Asn Ile Lys Pro Leu Glu Asp Lys
1               5

<210> SEQ ID NO 22
<211> LENGTH: 7
<212> TYPE: PRT
<213> ORGANISM: Homo sapiens

<400> SEQUENCE: 22

Met Phe Tyr Asn Gln Tyr Arg
1               5
```

POINT OF CARE ASSAYS TO DETECT THE STATUS OF TUBERCULOSIS INFECTION

CROSS-REFERENCE TO RELATED APPLICATIONS

This application claims priority from U.S. provisional applications 61/984,606 filed 25 Apr. 2014 and 61/949,857 filed 7 Mar. 2014. The contents of these documents are incorporated herein by reference.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 655652005100SeqList.txt, date recorded: May 19, 2015, size: 3,820 bytes)

TECHNICAL FIELD

The invention is in the field of diagnostics that are capable of performance at a point of care (POC). The assays detect peptides that appear in biological fluids of individuals at various types and stages of tuberculosis infection.

BACKGROUND ART

Currently available tests for tuberculosis infection are not satisfactory especially in remote areas or developing countries. Smear microscopy which is the primary tuberculosis (TB) diagnostic in much of the world requires training to be performed successfully and it is not always possible to find adequately trained personnel. Chest X-rays are not specific for TB and, of course, require special equipment.

The purified protein derivative (PPD) assay relies on a delayed hypersensitivity reaction to the infectious tuberculosis bacterium (Mtb) antigens that takes 48-72 hours to develop, and cannot distinguish active from latent infection. GeneXpert™ and other genetic based tests are expensive as they rely on complex equipment in clinical laboratory settings.

The status of tuberculosis in individuals who are infected varies. About two-thirds of people that are exposed to Mtb may never show any sign of infection and fail to develop a positive test such as PPD, and at least some of them develop transient T-cell interferon gamma responses to Mtb antigens. In a second group, the Mtb survive and multiply to elicit a long-lived adaptive immune response which is reflected in a positive PPD test. About 90% of these never develop active disease. This is the group of individuals that are latently infected. About 10% of these infected individuals develop active TB.

It is important to distinguish between these types of tuberculosis, as well as to identify all those who have been infected as the spread of the disease is caused by exposure to aerosols from infected individuals. Those with latent TB or who are resistant may cause infection in others. Thus, there is a need for a test that can readily detect not only whether the individual is infected, but also is able to determine the nature of the progress of the infection.

Napolitano, D. R., et al., *Clinical and Vaccine Immunology* (2008) 151:638-643, suggest the Mtb protein ornithine carbamoyl transferase, the product of MT_1694 gene, in urine, as a candidate indicator for detecting active T B. Kashino, S. S., et al., *Clinical and Experimental Immunology* (2008) 153:56-62, add the products of MT_1721, MT_2462 and MT_3444 as candidates.

DISCLOSURE OF THE INVENTION

A number of peptides derived from Mtb proteins have now been identified that are present in the biological fluids of individuals infected with tuberculosis wherein the pattern of peptides present in particular biological fluids is also indicative of the type of response the subject has to the bacterium. Thus, the "status" of tuberculosis infection, as defined herein, includes not only the probability of whether or not infection is present, but also the probability that the individual is virtually permanently resistant, or is experiencing a latent form of infection or has active TB.

Thus, in one aspect, the invention is directed to a method to identify the status of tuberculosis infection in a subject which method comprises detecting the presence or absence and/or amount of the invention peptides in a biological fluid of a subject. The presence of said peptides indicates the probable presence of infection, and a quantitative measure of the peptides indicates the probable nature of the infection in the subject. Higher amounts indicate more active infection. The invention is also directed to isolated forms of these unique peptides themselves.

In some embodiments, the detecting is of complexes formed by the peptides of the invention with affinity reagents that bind specifically therewith. Thus, the invention is also directed to assays for the peptides of the invention where the presence of complexes with the affinity reagents form the basis for concluding that the subject is infected by tuberculosis and the quantity of these complexes is an index of the nature of the infection—e.g., latent, active or that in a subject showing resistance.

As assay methods require affinity reagents such as aptamers, antibody mimetics, antibodies or immunoreactive fragments of antibodies directed against these peptides, in another aspect, the invention is directed to affinity reagents such as antibodies or fragments.

The invention also includes kits and formats for conducting the methods of the invention. In some embodiments, the kits include the isolated peptides as positive controls. Reagents specifically reactive with the peptides of the invention may be present in such kits attached to solid supports, in some instances, in an orderly array when two or more reagents are employed in the assay. Lateral flow formats are included as a desirable embodiment.

The subjects may be any animal that is subject to tuberculosis infection as well as humans and the biological fluids are those that are readily obtainable such as blood, plasma, urine or sputum. Such animals include canine, feline and bovines, as well as ovine and porcine subjects amongst others.

MODES OF CARRYING OUT THE INVENTION

Figure 1:
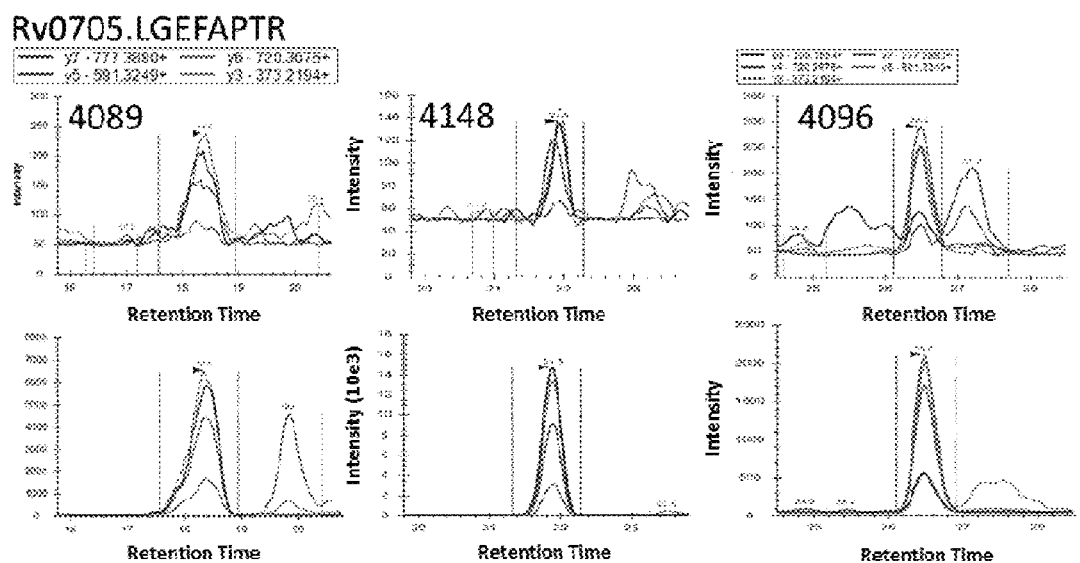
FIG. 1 shows typical results from SRM-MS from 3 patients with regard to the presence of the peptide LGE-FAPTR.

As used herein "a" "an" and the like refer to one or more than one unless it is clear from the context otherwise. All documents cited herein are incorporated by reference.

Applicants have identified 22 specific peptides whose presence or absence and/or amount in a bodily fluid of a subject can be used to determine the status of tuberculosis infection. These peptides are among a multitude of possible Mtb peptides and applicants have verified their relationship to not only whether the subject is infected with the tuberculosis bacterium but also the nature of the infection as described above. Thus, the term "status" is used to refer not only to the presence or absence of infection, but also whether the infection is latent, resisted, or active.

These assays, because they are based on the presence of peptides, can be adapted to simple performance by individuals who lack extensive training at a point of care (POC), even in difficult environments. This is especially important since tuberculosis appears to be problematic, particularly in these environments.

As it is the peptides themselves that are indicative of Mtb status, the methods of the invention do not exclude sophisticated methods such as HPLC/MS and flow cytometry or even complex proteomics. However, the invention is particularly significant because it can be adapted to POC formats.

Thus, the assays of the invention are typically designed to be sufficiently simple to be performed at the POC. In one embodiment, these are immunoassays which can be performed in a variety of formats, including ELISA, fluorescence detection, radioisotope detection, and the like. Other formats require reagents such as aptamers. While more sophisticated methods, such as flow cytometry are also applicable and included in the invention, these are not necessary in order to conduct the method and are generally inconvenient in a point of care situation.

The invention includes any method to assess the presence or absence and/or quantity of the unique peptides shown by applicants to be associated with the status of tuberculosis, including sophisticated methods such as flow cytometry, HPLC/mass spectrometry, and the like. While the focus is to develop assays that are suitable as POC performance assays which require little or no training on the part of the worker conducting the assays, the invention is importantly associated with the identification of these critical peptides that were hitherto unknown markers of tuberculosis status. The status with regard to the presence or absence of infection by Mtb per se is indicated by the presence or absence of one or more of the invention peptides. The nature of the status is further elucidated by the quantitation of one or more of these peptides, including elucidating the status of resistance, latency or active infection.

In the assays of the invention, the presence or absence and/or quantity of peptides may reside in one peptide of the 22 listed in Table 1, or two or more. Thus, depending on the precision required, detection may be based on two or more, three or more, four or more, etc., of the peptides. The invention includes methods whereby any integral number between 1 and 22 of the listed peptides is detected or measured.

The format of the assay can vary including sandwich type assays, lateral flow assays, homogeneous assays, and the like. A multiplicity of methods is known in the art for detection of complexes formed between an affinity reagent such as an antibody or its immunoreactive fragment and the appropriate peptide.

Applicants have found that the presence of certain peptides in the biological fluids of a subject indicate a high probability that the subject is infected with tuberculosis. The following table shows the Rv number, gene name, protein and functional category according to Tuberculist located on the World Wide Web at tuberculist.epfl.ch/. The invention peptides are of SEQ ID NOS:1-22 as follows:

TABLE 1

| Rv No. | Gene name | Peptide | Protein | SEQ ID NO: | plasma | urine | sputum |
|---|---|---|---|---|---|---|---|
| 0036c | | AESDDLDALVAHLPADR | Conserved protein | 1 | | | X |
| 0053 | rpsF | AAPATVSELDR | 30S ribosomal protein S6 | 2 | X | X | |
| 0166 | fadD5 | ALEIVDALPR | Probable fatty-acid-CoA ligase FadD5 | 3 | X | X | |
| 0167 | yrbE1A | MCVLTGK | Conserved integral membrane protein | 4 | | X | |
| 0169 | mce1A | NFYDADPLAK | Mce-family protein | 5 | X | X | |
| 0170 | mce1B | VELDDLLHK | Mce-family protein | 6 | X | | X |
| 0171 | mce1C | FSIGTNTIGTESR | Mce-family protein | 7 | X | | X |
| 0379 | secE2 | DSVDDIR | Possible protein transport protein | 8 | X | X | |
| 0566c | | AFEAGEPQASGK | Conserved protein | 9 | X | | X |
| 0682 | rpsL | VYTTTPK | 30S ribosomal protein S12 | 10 | | | X |
| 0703 | rplW | DIILAPVISEK | 50S ribosomal protein L23 | 11 | X | X | |
| 0705 | rpsS | LGEFAPTR | 30S ribosomal protein S19 | 12 | X | | X |
| 0706 | rplV | ATEYPSAVAK | 50S ribosomal protein L22 | 13 | X | | X |
| 0709 | rpmC | EELFNLR | 50S ribosomal protein L29 | 14 | X | | X |

TABLE 1 -continued

| Rv No. | Gene name | Peptide | Protein | SEQ ID NO: | plasma | urine | sputum |
|---|---|---|---|---|---|---|---|
| 1397c | vapC10 | DWLVSAR | Possible toxin | 15 | X | | X |
| 2245 | kasA | VAGCDQAAVYAPK | 3-oxoacyl-[acyl-carrier protein] synthase 1 | 16 | X | X | |
| 2474c | | LSDSPLQVTIWTK | Conserved hypothetical protein | 17 | X | | |
| 2866 | relG | ELAGTFSAR | Toxin | 18 | X | | |
| 3028c | fixB | VSAELITAAR | Probable electron transfer flavoprotein (α-subunit) | 19 | X | | X |
| 3150 | nuoF | SFCALGDGAASPVMSSIK | Probable NADH dehydrogenase I (chain F) | 20 | X | | X |
| 3418c | groES | VNIKPLEDK | 10 kDa chaperonin | 21 | X | | X |
| 3803c | fbpD | MFYNQYR | Secreted MPT51/MPB51 antigen protein | 22 | | | X |

The X values in the vertical columns indicate the presence of the peptide, as determined in Example 1 below.

Sample Preparation

Specific techniques have been developed to prepare samples derived from various biological fluids for testing. It is important to maintain the safety of these samples, especially in the case of sputum which may contain the infectious agent itself. The integrity of the proteins in the samples must also be preserved. The techniques that are favorable for preparation of the final material to be tested are described as follows. They are set forth in the past tense as these preparation methods have actually been performed, and they serve as guidance for the practice of the invention.

Plasma:

Samples were collected in P800 plasma preparation tubes (B/D, USA) to preserve proteins from proteolytic degradation. Plasma was initially processed by depleting the sample of the 14 most abundant blood proteins using an Agilent-14 MARS column (Agilent technologies, USA) before proceeding with reduction and alkylation with DTT/iodoacetamide and tryptic digestions. After desalting and buffer exchange, the samples were lyophilized, and the peptides obtained were analyzed by selected reaction monitoring (SRM) MS.

Sputum:

A BSL3 laboratory was used to contain and decontaminate the samples to ensure no live Mtb was released by further sample processing. Samples were decontaminated by bead beating in 8 M GnHCl, 0.2 μm filtered, reduced with 10 mM DTT and the free-SH was alkylated with 50 mM iodoacetamide. Once complete the sample was tested for live Mtb by culture and if negative, taken out of the BSL3 laboratory and further processed to obtain tryptic peptides. After desalting and buffer exchange, the samples were lyophilized, and the peptides obtained were analyzed by SRM MS.

Urine:

Undiluted urine was subjected to 50 kDa MWCO filter preparation. This was followed by reduction and alkylation with DTT/iodoacetamide and desalting using a G25 column. The G25 column step was necessary to purify proteins from low MW compounds such as urobilin that will foul the mass spectrometer during SRM assays. After desalting and buffer exchange, the samples were lyophilized, tryptic digested and the peptides obtained were analyzed by SRM MS.

Affinity Reagents

The affinity reagents useful in the invention include any reagents that are specifically reactive with and bind specifically to the peptides identified above. While antibodies or their fragments are very convenient as such reagents, as further discussed below, other affinity reagents useful in the invention are also included. Such reagents include, for example, aptamers and artificially synthesized mimetics of antibodies or aptamers.

Thus, other "non-antibody" affinity reagents such as peptide based affinity binders DNA aptamers or chimeric molecules with sufficient affinity to the peptides described here can also be used to develop a POC device where these non-antibody binders can be labeled for ease of detection and reporting.

Literature describing these alternatives include, for example, Williams, B. A., et al., *Am. Chem. Soc.* (2009) 131:17233-17241. doi: 10.1021/ja9051735.PMID: 19894711; Brody, E. N., et al., *Mol. Diagn.* (1999) 4:381-388 PMID: 10671648; Righetti, P. G., et al., *Proteomics* (2006) 14:3980-3992. Review. PMID: 16800034.

Antibodies

For point of care designs, a convenient format for assessing the peptides of the invention is immunoassays. If this is to be the case, the invention peptides are used to generate polyclonal and/or monoclonal antibodies using standard techniques, including immunization of typical responders such as rabbits, mice and the like. As the antibodies are to be used diagnostically ex vivo, the subject of the immunization need not be the same as the subject for whom diagnosis is performed. In some embodiments of the invention, polyclonal antibodies that are immunoreactive with the peptide target can be used. These can be purified from the plasma of the immunized subject using known techniques such as affinity chromatography and the like.

In addition, monoclonal antibodies can be prepared using standard techniques from the spleens or peripheral blood cells of the immunization subject and can be produced recombinantly by isolating the encoding nucleic acids from cells that have been identified as secreting the desired antibodies. Methods for identifying these cells are well known in the art and include sophisticated methods such as those set forth in U.S. Pat. Nos. 7,413,868 and 7,939,344 which are highly efficient at determining, from millions of cells, those that secrete antibodies with the desired specificity. Other methods for obtaining antibodies that are immunospecific for desired peptides and recombinant materials for their production are described in Cheung, W. C., et al., *Nature Biotech*. (2012) 30:447-452 and online Supplementary Materials. This method relies on matching immunoreactive antibodies generated by immunization of an animal with appropriate variable chain sequences from the B cell repertoire of the immunized animal.

Any method of generating monoclonal antibodies can be used, including traditional methods employing hybridoma technology.

It is desirable that the antibodies used in the method are immunoreactive exclusively with the peptide used as immunogen and do not react with the corresponding protein. Table 1 above sets forth the corresponding proteins for the peptides of the invention.

As used herein "antibodies" includes fragments of the antibodies that are immunoreactive with the peptides of interest as well as various forms of recombinantly produced antibodies such as single chain antibodies, and complete antibody or fragments that are recombinantly prepared. Thus, Fab, $F(ab)_2$, $F_v$, Fsv, diabody, etc., types are included in the definition of antibodies whether or not specifically set forth.

Assays

The assay may be conducted using, and the invention is directed to, one or more reagents that specifically bind 1-22 of the listed peptides and all intervening integers. The one or more affinity reagents may be coupled to one or more solid supports. In one embodiment, arrays or panels of two or more reagents may be used in this or other formats. In some formats, a solid support may be coupled only to a single reagent, and in some formats in general, only a single reagent may be used. If a panel or array of two or more reagents, whether or not coupled to a solid support is used in the assay, the reagents may be specific for one or more than one of these peptides. The panel or single reagent can be packaged into a kit which may also contain one or more of the 22 peptides listed above as a positive control. In some formats, that peptide is also coupled to a solid support.

Lateral flow formats appear particularly attractive for POC assays as they are readily conducted and are compactly packaged. Such formats are well known and are typically used, for example, in over-the-counter pregnancy assays.

There are many designs available for lateral flow assays. In general, such assays comprise a porous support strip such as of cellulose with a number of separate regions spaced horizontally along the support. The solid support need not be identical in all regions of a strip. Typically, the first region is a sample pad where a biological fluid may be applied to flow laterally through the support to the remaining regions. The second region generally contains a labeling moiety that can be bound to the peptide in the sample if any is present. Downstream of the labeling region is a capture or "test" region where the labeled peptide is retained in the strip. It is in this test region where detection is generally done. In addition to the test region, the strip may contain a control region either in the same flow path as that of the test region, or in a parallel path on the strip. There may also be a reservoir downstream of the various regions to absorb the sample that has traversed the test strip.

The control feature may be structured in a number of ways, including supplying a known amount of the peptide itself in the sample pad or an adjacent sample pad so that it will be clear that the test reaction is working properly. Alternatively, a control strip may be located downstream from the third region and formatted so as to register a positive response simply in response to the flow of fluid. The control region downstream from the capture region for the labeled peptide may contain, for example, reagents that will capture excess conjugating label. Thus, for example, the capture reagents in the test region will bind to a sequence in the peptide different from the binding of the labeling reagent and the control region will bind to the labeling reagent itself.

Alternatively, a parallel control strip on the same solid support can be formatted.

Assays conducted in this format may be direct assays forming sandwiches in proportion to the level of analyte present, or may be competition assays where analyte in the sample diminishes the amount of label detected in the detection zone. In direct sandwich assays, for example the sample may be labeled by colored particles that are coupled to affinity reagents such as antibodies immunoreactive with the peptides forming complexes which are then carried to the test region for capture by an additional reagent. The detectable label in the test region will be directly proportional to the level of peptide in the sample.

In competitive assays, the labeling region may contain labeled reagents, for example, which are already coupled to the target analyte or an analog thereof, and the peptides in the sample compete with this labeled material for capture by the capture reagent in the test region. In this case, the detectable label in the test region will be inversely proportional to the quantity of peptide in the sample itself.

While simple visual detection is the most common means of reading the assay, there are commercially available lateral flow readers that can quantitate the detectable label in the test region.

In some cases, it is advantageous to use polyclonal antibodies as either the labeling or capture reagent as a multiplicity of epitopes are bound by the polyclonals.

Further, in lateral flow assays, it is possible to set up parallel assays for a multiplicity of the peptides of the invention, either on a single strip where the lanes are run in parallel or on separate strips. All of these components may be included in kits for conducting these assays in the field.

The following example is intended to illustrate but not to limit the invention. It demonstrates the validity of the various peptides as markers for tuberculosis whether latent or active and employs techniques for identification of the relevant peptide markers which can be considered part of the invention, but typically would not be those performed in a point-of-care context. Thus, the design of point-of-care assays, as a significant contribution of the invention would typically employ the techniques and reagents described hereinabove.

Example 1

Determination of Peptide Markers in Tubercular Patients

Sixty-five (65) patients who were TB suspects and being treated for tuberculosis were used in this study. Healthy controls were subjected to the same assay and did not display any of the peptides found in the TB suspect patients described in the assays below. This is expected as the peptides are hydrolysis products of Mtb peptides.

Samples of plasma, sputum and urine from each of these 65 patients were obtained as described above with respect to sample preparation. The samples prepared as described were analyzed by highly standardized SRM mass spectrometry with a chip-based column set-up using an Agilent 6460 QQQ mass spectrometer. SRM assays were conducted in scheduled mode so that multiple SRM assays were programmed into each run separated by windows to increase the multiplexing capability of SRM analysis. The results of the analyses are shown in Table 1 above, where the X in each column indicates the presence of the peptide.

Figure 2:
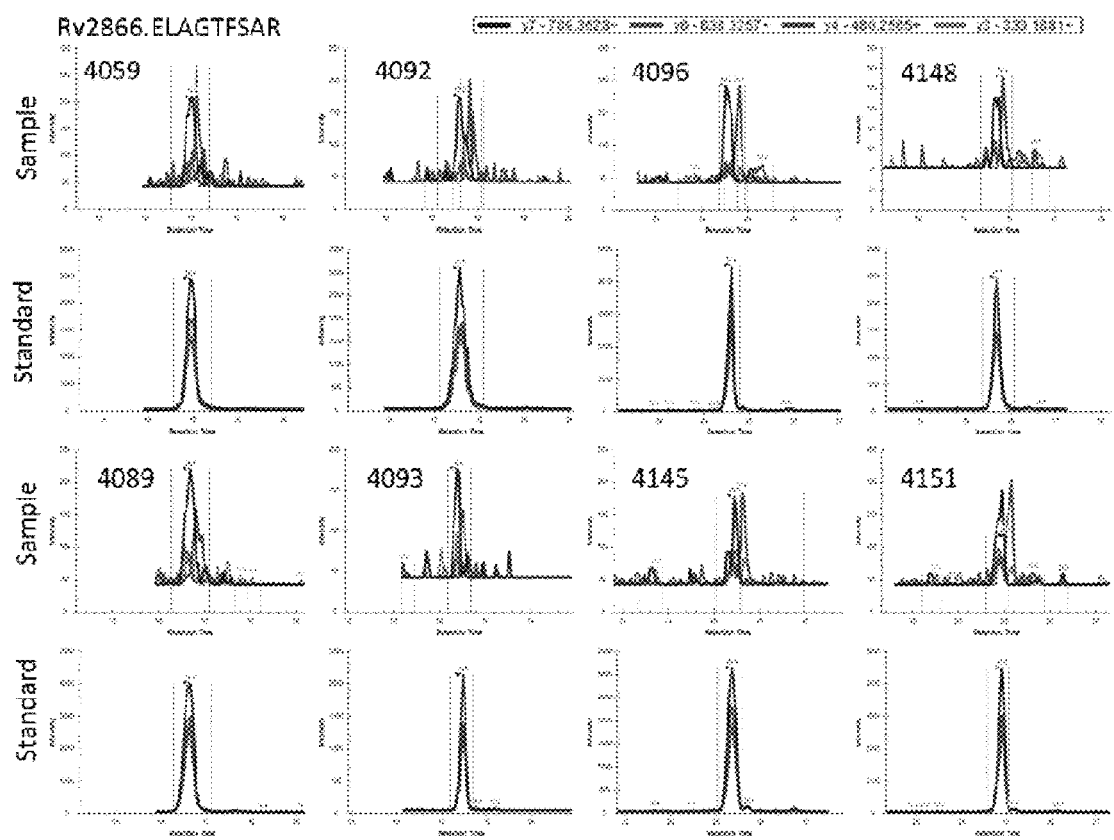
FIG. 2 shows typical results from 8 patients with regard to the presence of the peptide ELAGTFSAR.

Typical results for exemplary peptides are shown in FIGS. 1 and 2. As shown in FIG. 1, the exemplary peptide LGEFAPTR is confirmed in patients 4089, 4148 and 4096 by the relevant confirmatory peaks at the appropriate retention times of the chromatography feed to the mass spectrometer. As shown in FIG. 2, similar results for the peptide ELAGTFSAR in 8 different patients are confirmed by a similar comparison with standards.

Figure 3:
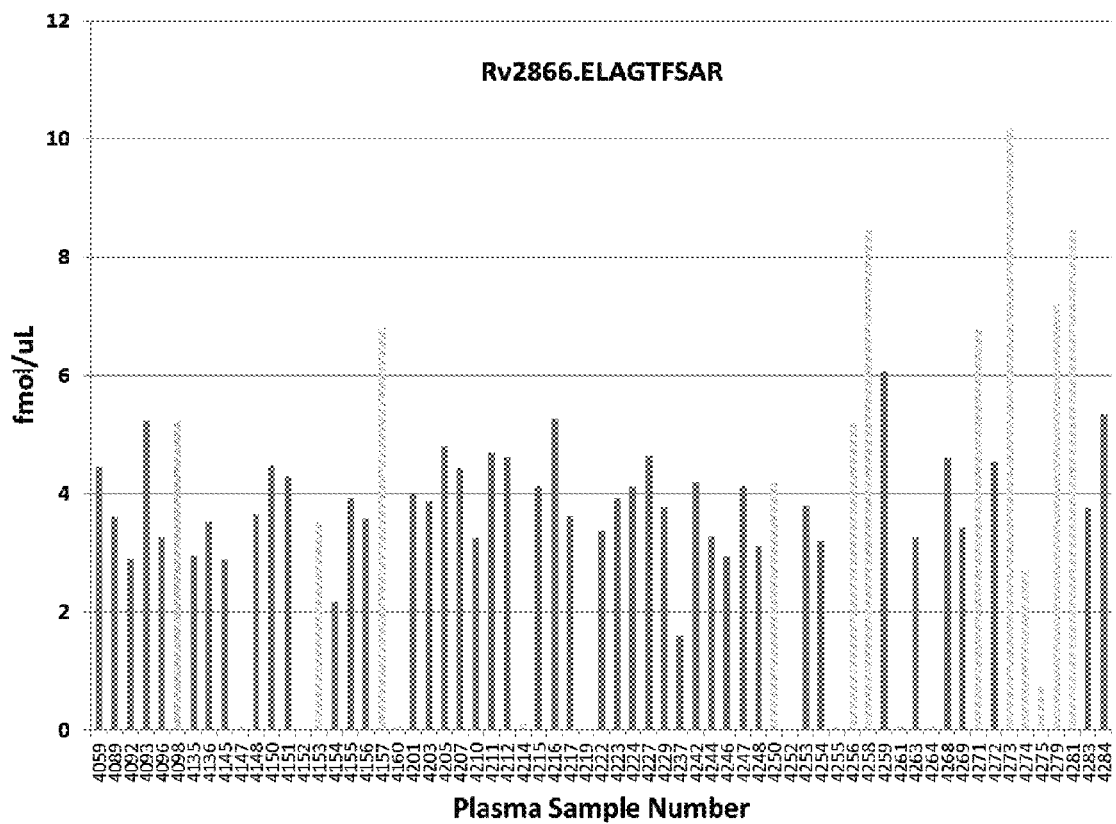
FIG. 3 shows a summary of the results obtained in plasma of all 65 patients suspected of having tuberculosis infection with respect to elevation of ELAGTFSAR in the plasma samples.

Finally, FIG. 3 shows a summary of the results for detecting the exemplary peptide ELAGTFSAR in plasma over the entire group of 65 patients showing the concentration in fmol/µl. The solid lines indicate a confirmed presence whereas the dotted lines indicate a tentative identification. As shown, a few of the patients did not exhibit the presence of these peptides, and thus they test as tuberculosis-free.

The invention claimed is:

1. A method to identify the probable status of tuberculosis infection in a subject which method comprises
   (a) preparing a tryptic digest of proteins in a sample of a biological fluid from said subject, wherein said tryptic digest may include at least one tryptic peptide selected from the group consisting of AESDDLDALVAHLPADR (SEQ ID NO:1); AAPATVSELDR (SEQ ID NO:2); ALEIVDALPR (SEQ ID NO:3); MCVLTGK (SEQ ID NO:4); NFYDADPLAK (SEQ ID NO:5); VELDDLLHK (SEQ ID NO:6); FSIGTNTIGTESR (SEQ ID NO:7); DSVDDIR (SEQ ID NO:8); AFEAGEPQASGK (SEQ ID NO:9); VYTTTPK (SEQ ID NO:10); DIILAPVISEK (SEQ ID NO:11); LGEFAPTR (SEQ ID NO:12); ATEYPSAVAK (SEQ ID NO:13); EELFNLR (SEQ ID NO:14); DWLVSAR (SEQ ID NO:15); VAGCDQAAVYAPK (SEQ ID NO:16); LSDSPLQVTIWTK (SEQ ID NO:17); ELAGTFSAR (SEQ ID NO:18); VSAELITAAR (SEQ ID NO:19); SFCALGDGAASPVMSSIK (SEQ ID NO:20); VNIKPLEDK (SEQ ID NO:21); and MFYNQYR (SEQ ID NO:22);
   (b) contracting said digest with at least one affinity reagent that binds at least one said peptide,
   (c) detecting the presence or absence of a complex of any said tryptic peptide in said digest formed by reaction with the affinity reagent;
   thereby detecting the presence or absence and/or quantity of the peptide in said digest;
   whereby the probable status of tuberculosis infection in said subject is identified.

2. The method of claim 1, wherein the affinity reagent is an antibody or an aptamer.

3. The method of claim 1, wherein said digest is contacted with at least four of said reagents.

4. The method of claim 1, wherein the presence or absence of said complex is detected by fluorescence labeling, enzyme activity labeling, or radioactive isotope labeling.

5. The method of claim 1, wherein the complex is detected by flow cytometry.

6. The method of claim 1, wherein the complex is formed in a sandwich assay.

7. The method of claim 1, wherein the complex is formed in a lateral flow assay.

8. The method of claim 1, wherein the subject is human.

9. The method of claim 1, wherein the biological fluid is blood, plasma, urine or sputum.

10. The method of claim 9 wherein the biological fluid is plasma and the at least one peptide is selected from the group consisting of AAPATVSELDR (SEQ ID NO:2); ALEIVDALPR (SEQ ID NO:3); NFYDADPLAK (SEQ ID NO:5); VELDDLLHK (SEQ ID NO:6); FSIGTNTIGTESR (SEQ ID NO:7); DSVDDIR (SEQ ID NO:8); AFEAGEPQASGK (SEQ ID NO:9); DIILAPVISEK (SEQ ID NO:11); LGEFAPTR (SEQ ID NO:12); ATEYPSAVAK (SEQ ID NO:13); EELFNLR (SEQ ID NO:14); DWLVSAR (SEQ ID NO:15); VAGCDQAAVYAPK (SEQ ID NO:16); LSDSPLQVTIWTK (SEQ ID NO:17); ELAGTFSAR (SEQ ID NO:18); VSAELITAAR (SEQ ID NO:19); SFCALGDGAASPVMSSIK (SEQ ID NO:20); and VNIKPLEDK (SEQ ID NO:21).

11. The method of claim 9 wherein the biological fluid is urine and the at least one peptide is selected from the group consisting of AAPATVSELDR (SEQ ID NO:2); ALEIVDALPR (SEQ ID NO:3); MCVLTGK (SEQ ID NO:4); NFYDADPLAK (SEQ ID NO:5); DSVDDIR (SEQ ID NO:8); DIILAPVISEK (SEQ ID NO:11) and VAGCDQAAVYAPK (SEQ ID NO:16).

12. The method of claim 9 wherein the biological fluid is sputum and the at least one peptide is selected from the group consisting of AESDDLDALVAHLPADR (SEQ ID NO:1); VELDDLLHK (SEQ ID NO:6); FSIGTNTIGTESR (SEQ ID NO:7); AFEAGEPQASGK (SEQ ID NO:9); VYTTTPK (SEQ ID NO:10); LGEFAPTR (SEQ ID NO:12); ATEYPSAVAK (SEQ ID NO:13); EELFNLR (SEQ ID NO:14); DWLVSAR (SEQ ID NO:15); VSAELITAAR (SEQ ID NO:19); SFCALGDGAASPVMSSIK (SEQ ID NO:20); VNIKPLEDK (SEQ ID NO:21); and MFYNQYR (SEQ ID NO:22).

* * * * *